(12) United States Patent
Itoh

(10) Patent No.: US 10,402,614 B2
(45) Date of Patent: Sep. 3, 2019

(54) SAMPLE PROCESSING APPARATUS AND SAMPLE PROCESSING METHOD

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 0 days.

(21) Appl. No.: 15/392,159

(22) Filed: Dec. 28, 2016

(65) Prior Publication Data

US 2017/0185815 A1  Jun. 29, 2017

(30) Foreign Application Priority Data

Dec. 28, 2015 (JP) ................. 2015-256331

(51) Int. Cl.
| | |
|---|---|
| *G06F 17/00* | (2019.01) |
| *G06F 19/00* | (2018.01) |
| *G06Q 30/00* | (2012.01) |
| *G06Q 90/00* | (2006.01) |
| *G06K 7/14* | (2006.01) |
| *G06K 17/00* | (2006.01) |
| *G01N 35/00* | (2006.01) |
| *G01N 35/04* | (2006.01) |
| *G01N 35/10* | (2006.01) |

(52) U.S. Cl.
CPC ..... *G06K 7/1413* (2013.01); *G01N 35/00613* (2013.01); *G06K 17/0022* (2013.01); *G01N 2035/00752* (2013.01); *G01N 2035/00831* (2013.01); *G01N 2035/0467* (2013.01); *G01N 2035/0493* (2013.01); *G01N 2035/1025* (2013.01)

(58) Field of Classification Search
USPC ..................... 235/375, 462.01, 385; 705/2, 3
See application file for complete search history.

(56) References Cited

U.S. PATENT DOCUMENTS

| | | | |
|---|---|---|---|
| 6,081,326 A | | 6/2000 | Rousseau et al. |
| 6,599,476 B1 | * | 7/2003 | Watson ............. B65G 47/1471 141/1 |
| 2003/0019797 A1 | * | 1/2003 | Yamamoto ............... B07C 5/18 209/592 |
| 2004/0005245 A1 | | 1/2004 | Watson et al. |
| 2007/0134131 A1 | | 6/2007 | Watson et al. |

(Continued)

FOREIGN PATENT DOCUMENTS

| | | |
|---|---|---|
| CA | 2 882 339 | 2/2014 |
| CN | 1234870 | 11/1999 |

(Continued)

OTHER PUBLICATIONS

Extended European Search Report issued in Appln. No. 16205504.0 dated May 30, 2017.

(Continued)

*Primary Examiner* — Tuyen K Vo
(74) *Attorney, Agent, or Firm* — Nixon & Vanderhye P.C.

(57) ABSTRACT

According to an embodiment, a sample processing apparatus includes an image capture unit which captures an image of a sample container, and a sorting unit which performs a sorting process for the sample container based on a type of the sample container detected from the image.

12 Claims, 6 Drawing Sheets

(56) References Cited

U.S. PATENT DOCUMENTS

| | | | | |
|---|---|---|---|---|
| 2009/0003981 | A1* | 1/2009 | Miller | B65G 1/04 |
| | | | | 414/267 |
| 2010/0018330 | A1* | 1/2010 | Marty | G01N 35/00732 |
| | | | | 73/864.81 |
| 2010/0111384 | A1* | 5/2010 | Nagai | G01N 35/1011 |
| | | | | 382/128 |
| 2010/0111767 | A1* | 5/2010 | Yonekura | G01N 35/00732 |
| | | | | 422/65 |
| 2011/0173927 | A1 | 7/2011 | Yamada | |
| 2011/0245061 | A1* | 10/2011 | Haechler | B04B 13/00 |
| | | | | 494/8 |
| 2012/0275885 | A1* | 11/2012 | Furrer | G01N 35/00732 |
| | | | | 414/222.02 |
| 2013/0125675 | A1* | 5/2013 | Muller | B01D 21/262 |
| | | | | 73/864.23 |
| 2013/0130369 | A1* | 5/2013 | Wilson | B01L 3/5085 |
| | | | | 435/289.1 |
| 2013/0175342 | A1 | 7/2013 | Itoh | |
| 2013/0217141 | A1 | 8/2013 | Lenhard et al. | |
| 2013/0234053 | A1* | 9/2013 | Thomas | G01N 35/1011 |
| | | | | 250/573 |
| 2014/0087472 | A1* | 3/2014 | Kurono | G01N 35/00613 |
| | | | | 436/47 |
| 2014/0125797 | A1 | 5/2014 | Matsumoto et al. | |
| 2015/0241457 | A1* | 8/2015 | Miller | G01N 35/00732 |
| | | | | 348/143 |
| 2015/0346229 | A1 | 12/2015 | Furrer et al. | |
| 2016/0018427 | A1* | 1/2016 | Streibl | G01N 35/00584 |
| | | | | 702/19 |
| 2016/0025756 | A1 | 1/2016 | Pollack et al. | |
| 2018/0045654 | A1* | 2/2018 | Park | G01N 21/25 |

FOREIGN PATENT DOCUMENTS

| | | |
|---|---|---|
| CN | 102759630 | 10/2012 |
| CN | 103198312 | 7/2013 |
| CN | 103221827 | 7/2013 |
| CN | 103619251 | 3/2014 |
| EP | 0 479 622 | 4/1992 |
| JP | 2013-72806 | 4/2013 |
| TW | 201107212 | 3/2011 |
| TW | 201541081 | 11/2015 |
| WO | WO 2014/138533 | 9/2014 |

OTHER PUBLICATIONS

Canadian Office Action issued in Appln. No. 2,952,468 dated Sep. 14, 2017.
Taiwanese Office Action issued in Appln. No. 105143194 dated Sep. 18, 2017.
Chinese Office Action issued in Appln. No. 201611221491.8 dated Dec. 18, 2017 (w/ translation).
Korean Office Action issued in Appln. No. 10-2016-0179001 dated Apr. 6, 2018 (w/ translation).
Office Action issued in CA Appln. No. 2,952,468 dated Sep. 10, 2018.
Office Action issued in CN Appln. No. 201611221491.8 dated Sep. 11, 2018 (w/ translation).
Office Action issued in KR Appln. No. 10-2016-0179001 dated Sep. 18, 2018 (w/ translation).
Office Action issued KR Appln. No. 10-2016-0179001 dated Nov. 12, 2018 (w/ translation).
Office Action issued in CN Appln. No. 201611221491.8 dated Mar. 28, 2019 (w/translation).

* cited by examiner

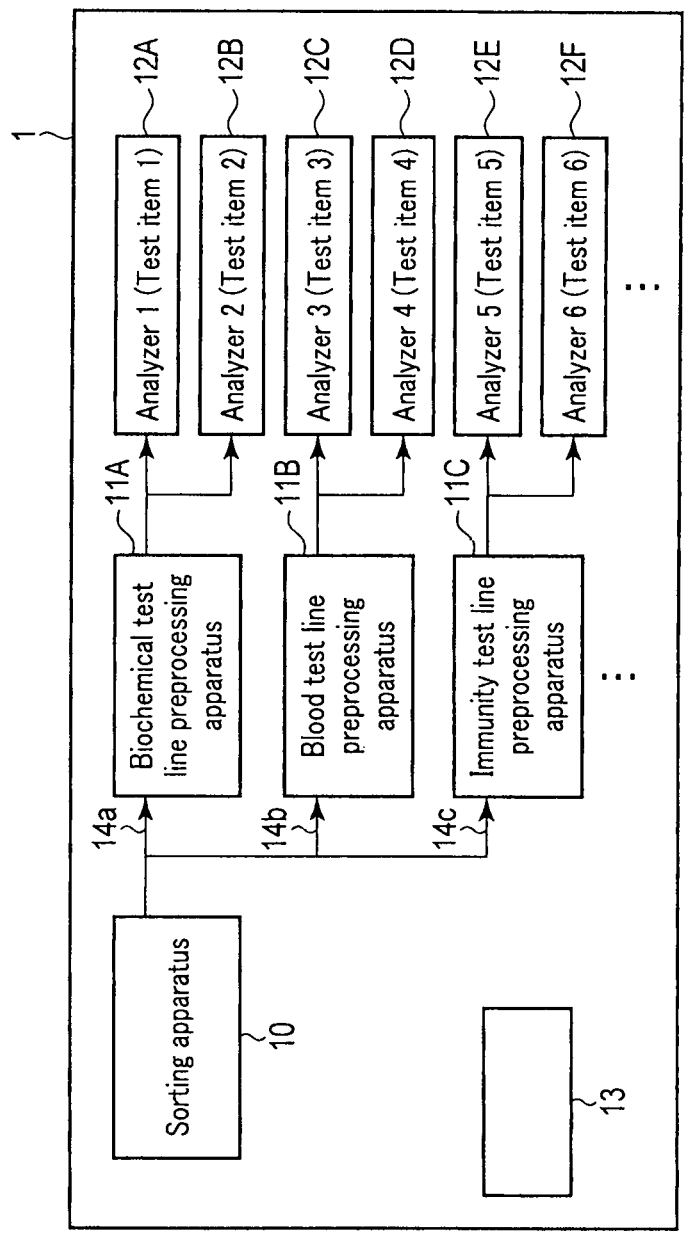
F I G. 1

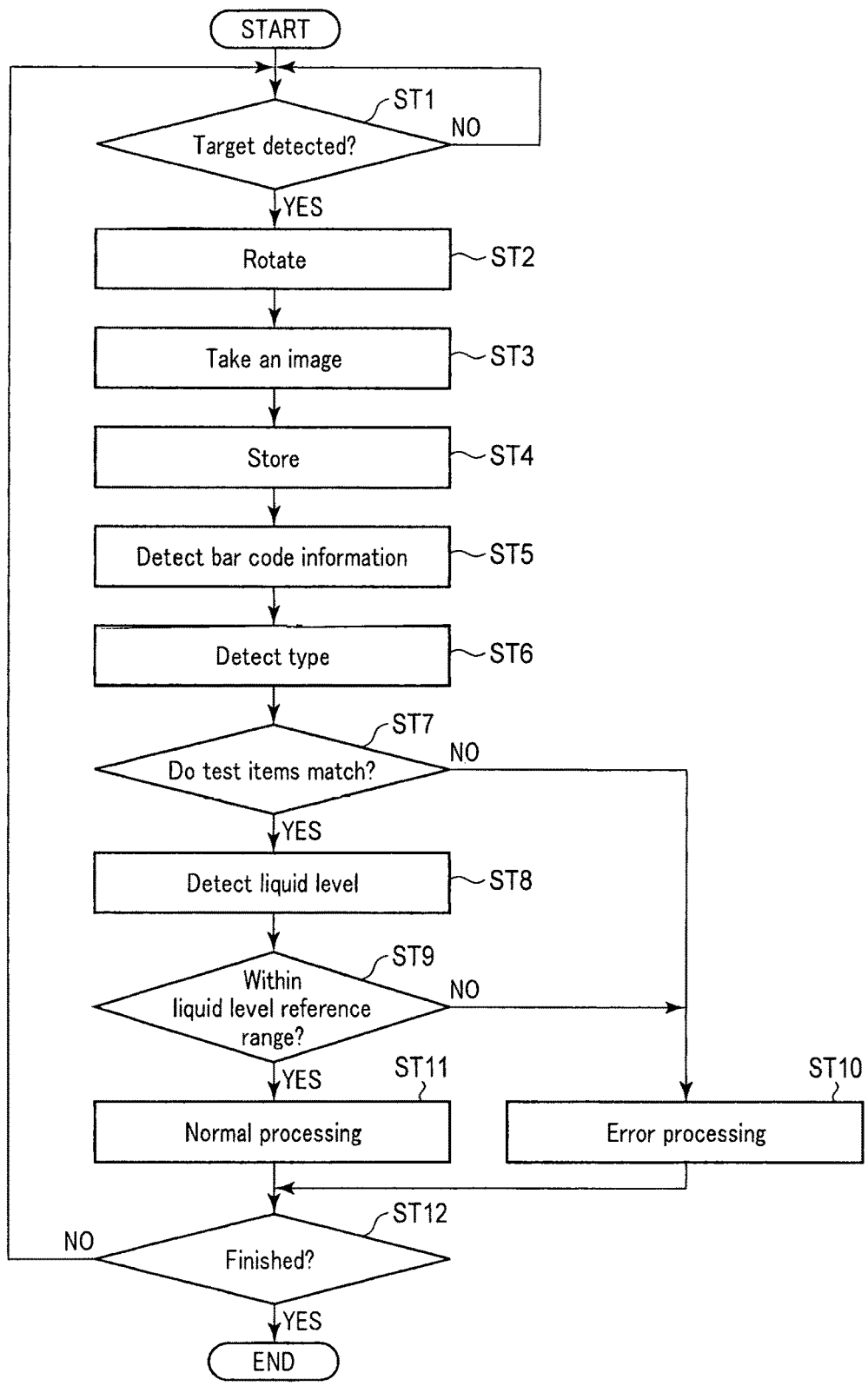
F I G. 3

FIG. 4

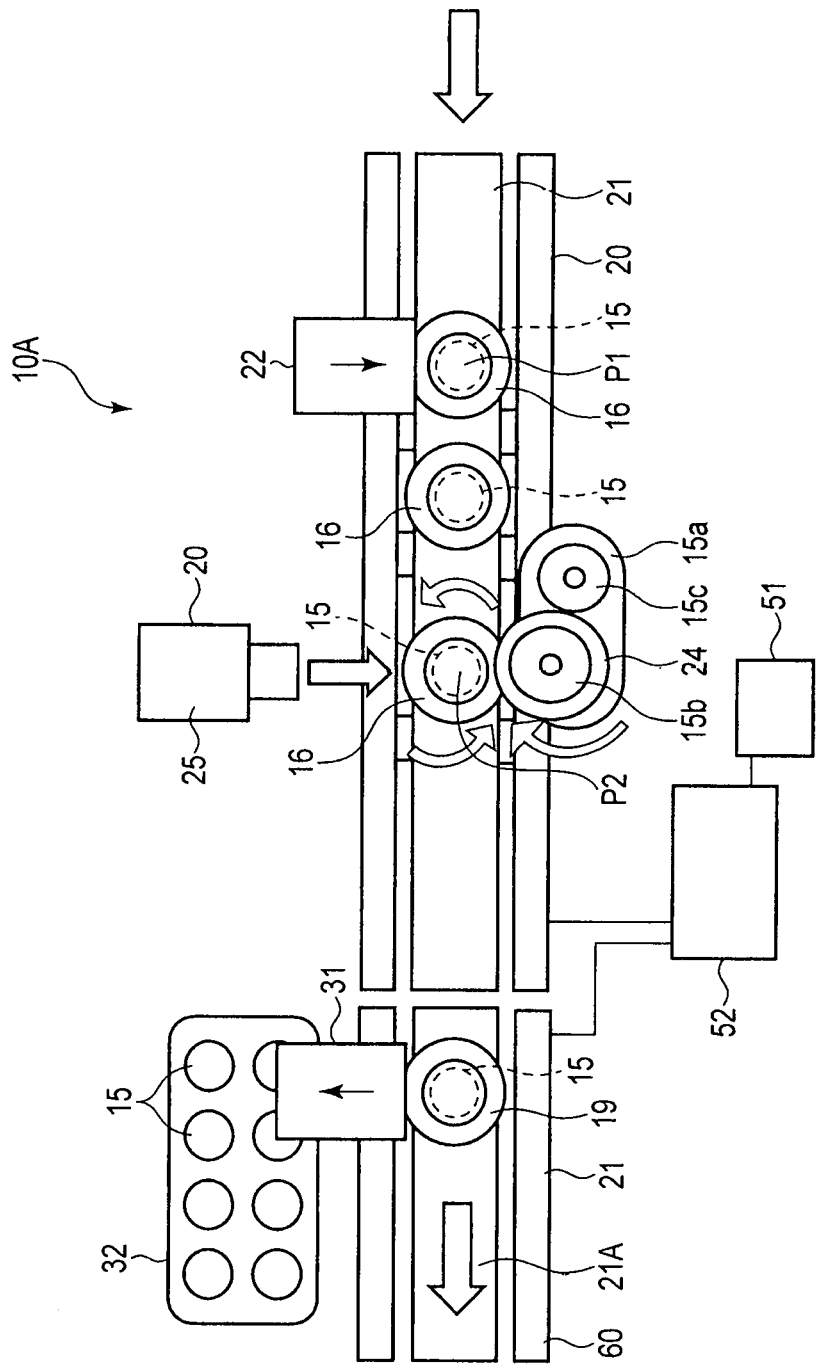
F I G. 6

SAMPLE PROCESSING APPARATUS AND SAMPLE PROCESSING METHOD

CROSS-REFERENCE TO RELATED APPLICATION

This application is based upon and claims the benefit of priority from the prior Japanese Patent Application No. 2015-256331, filed Dec. 28, 2015 the entire contents of them are incorporated herein by reference.

FIELD

The present invention relates to a sample processing apparatus for sorting samples and a sample processing method.

BACKGROUND

In a sample test, such as a test and an analysis of blood or blood serum, a sorting process to classify samples into a plurality of test items, for example, is carried out as preprocessing of such a sample test (Jpn. Pat. Appln. KOKAI Publication No. 2013-072806). For example, a label on which a test item and personal information are written is affixed on a sample container which stores a sample, and a bar code is read prior to a test in order to sort each of a plurality of sample containers into a carrier line of the test item corresponding to the bar code information.

If a wrong bar code is affixed to a sample container, for example, a problem arises wherein the sample container is sorted based on information of the wrong bar code. Accordingly, a sample processing apparatus and sample processing method that can improve the accuracy of a sorting process is desired.

SUMMARY

According to an embodiment, a sample processing apparatus comprises an image capture unit which captures an image of a sample container, and a sorting unit which performs a sorting process for the sample container based on a type of the sample container detected from the image.

The sample processing apparatus and the sample processing method according to the embodiments of the present invention can provide a sample processing apparatus and a sample processing method that can improve the accuracy of sorting.

BRIEF DESCRIPTION OF THE DRAWINGS

FIG. 1 is a block diagram showing the schematic structure of a sample processing unit according to one embodiment of the present embodiment.

FIG. 3 is a flowchart showing a control procedure of a sorting process according to the embodiment.

FIG. 4 is an explanatory drawing of a matching determination process in the sorting process.

FIG. 6 is a plan view showing the schematic structure of a sorting apparatus according to another embodiment of the present invention.

DETAILED DESCRIPTION

Figure 2:
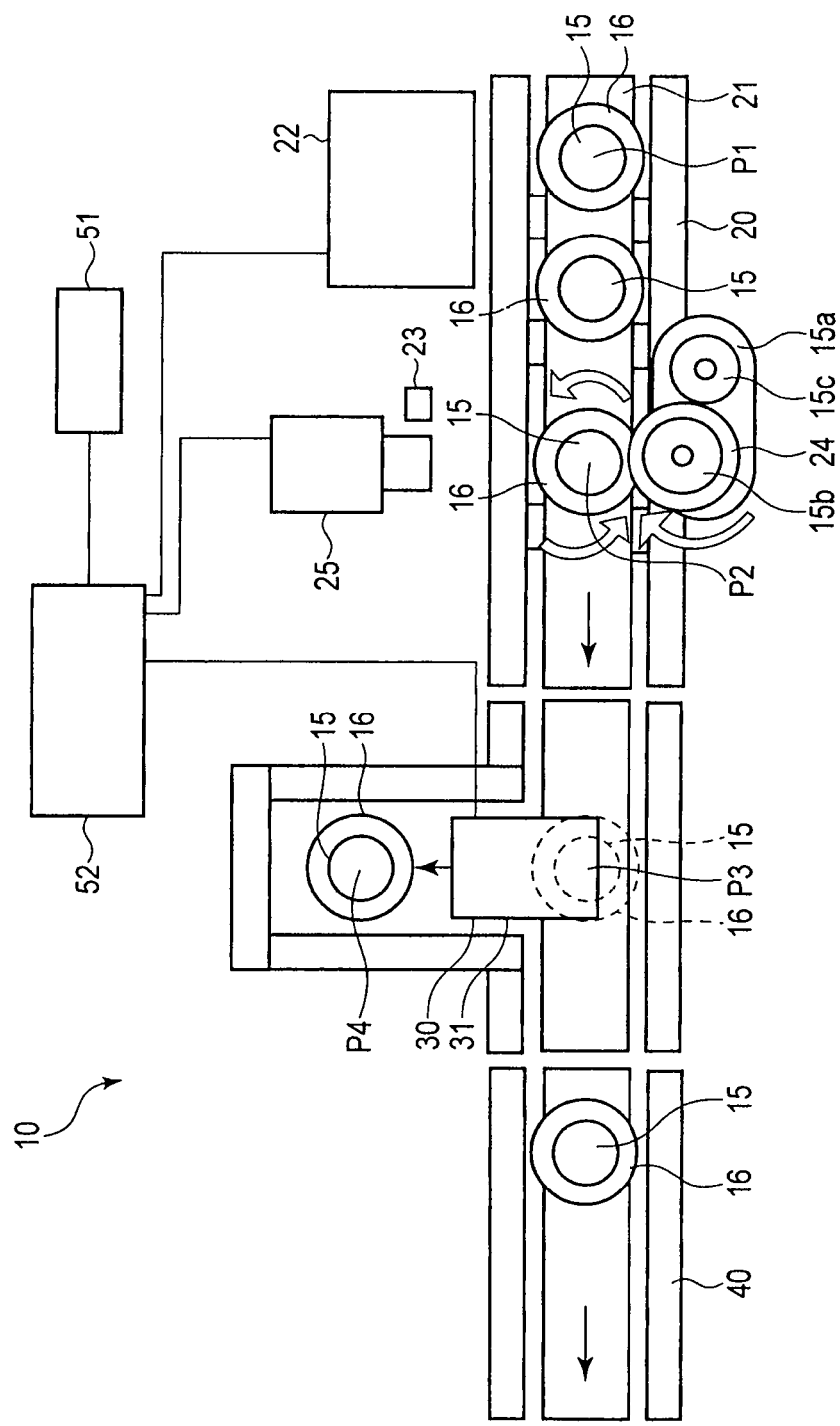
FIG. 2 is a plan view of the schematic structure of a test unit.

A sample processing unit, a sample processing apparatus, and a sample processing method according to one embodiment of the present invention will be described with reference to FIGS. 1 to 5. FIG. 1 is an explanatory drawing showing the structure of a test unit 1 as an example of a sample processing unit according to the present embodiment, and FIG. 2 is an explanatory drawing of a sorting apparatus 10 as an example of a sample processing apparatus. In each of the drawings, the structural elements are enlarged, reduced, or omitted as needed.

As shown in FIG. 1, the test unit 1 comprises a sorting apparatus 10 which is an example of the sample processing apparatus and sorts sample containers 15 for storing a sample into a plurality of test lines, a plurality of preprocessing apparatuses 11A to 11C provided respectively at a plurality of test lines 14a to 14c, a plurality of analyzers 12A to 12F which are provided on the downstream of respective preprocessing apparatuses and which respectively correspond to a plurality of test items, and a control apparatus 13 which controls the operation of each of the apparatuses.

In the present embodiment, three test lines 14a to 14c, a blood test, a biochemical test, and an immunity test, for example, are provided, and the analyzers 12A to 12F are respectively provided on the test lines 14a to 14c for two test item types. The number and types of the test lines 14a to 14c and of the analyzers 12A to 12F are not limited thereto.

The sorting apparatus 10 is an apparatus which captures an image of each of the sample containers 15 prior to various test processes on samples, distinguishes the test items based on display information and types from the image information, and sorts the sample containers 15 accordingly. In the present embodiment, a sorting process for one of the test lines 14a to 14c, for example, the biochemical test line 14a, is described as an example.

As shown in FIG. 2, in the sorting apparatus 10, units 20, 30, and 40, each configured as a separate apparatus and comprising a carrier path above the apparatus itself, are arranged side by side in such a manner that their carrier paths are to be continuous. The sorting apparatus 10 comprises three units, that is, an image capture unit 10 which comprises a carrier mechanism 21 and captures an image of the sample container 15 at an imaging position P2 on the carrier path, a sorting unit 30 which comprises the carrier mechanism 21 and removes from the carrier path an erroneous sample container 15 determined as a mismatch, and a continuation unit 40 which comprises the carrier mechanism 21 and sends, to a predetermined test line in the downstream, a sample container 15 determined as a match, and the sorting apparatus 10 further comprises a storage unit 51 which stores various information, and a CPU 52 which is a control section which performs calculation and determination based on various information and controls the operation of each section.

The image capture unit 20 comprises a conveyor-type carrier mechanism 21 which carries the sample container 15 in a standing state, a loading apparatus 22 which loads the sample container 15 at a loading position of the carrier path, a position sensor 23 which detects the position of the sample container 15, a rotation mechanism 24 which rotates the sample container 15 sent to the imaging position P2, and an imaging section 25 which takes an image of the sample container 15.

The carrier mechanism 21 is a conveyor-type carrier mechanism provided at the top of the apparatus, and it carries holders 16 for holding the sample containers 15 along a predetermined carrier path in a standing state. The carrier mechanism 21 comprises a pair of guide rails disposed with a certain width therebetween along the carrier path extending in a certain direction, a carrier belt arranged between the guide rails along the carrier path, and a drive section, such as a carrier roller, etc. which is rotatively driven at the back of the carrier belt to send the carrier belt.

The holder 16 holding the sample container 15 is engaged with the pair of guide rails and supported in a standing state, and it is carried along with the movement of the carrier belt.

The carrier path is a predetermined route to the test lines 14a to 14c through the loading position P1 and the imaging position P2. A processing apparatus which performs a variety of processes on the samples 18 or the sample containers 15 is provided along the carrier path.

The loading apparatus 22 comprises a transfer mechanism which grips the sample container 15 arranged, for example, in an external rack, etc., and which subsequently inserts the sample container 15 into the holder 16 waiting at the loading position P1 on the carrier line. The transfer mechanism repeats an operation of loading the sample container 15 at a predetermined timing in accordance with the control at the CPU 52, for example, to put a plurality of the sample containers 15 on the carrier path one after another.

Figure 4:
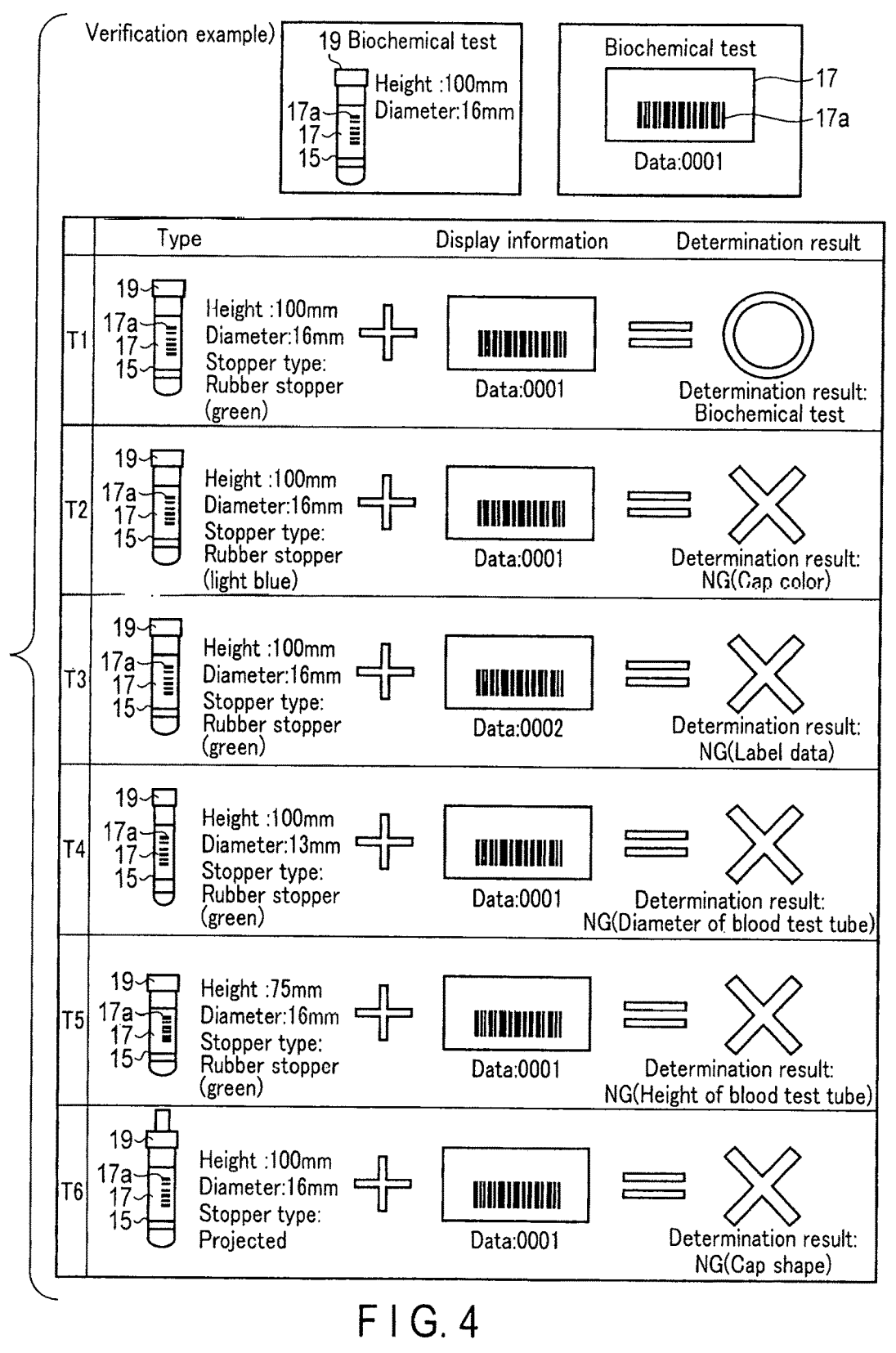
Figure 5:
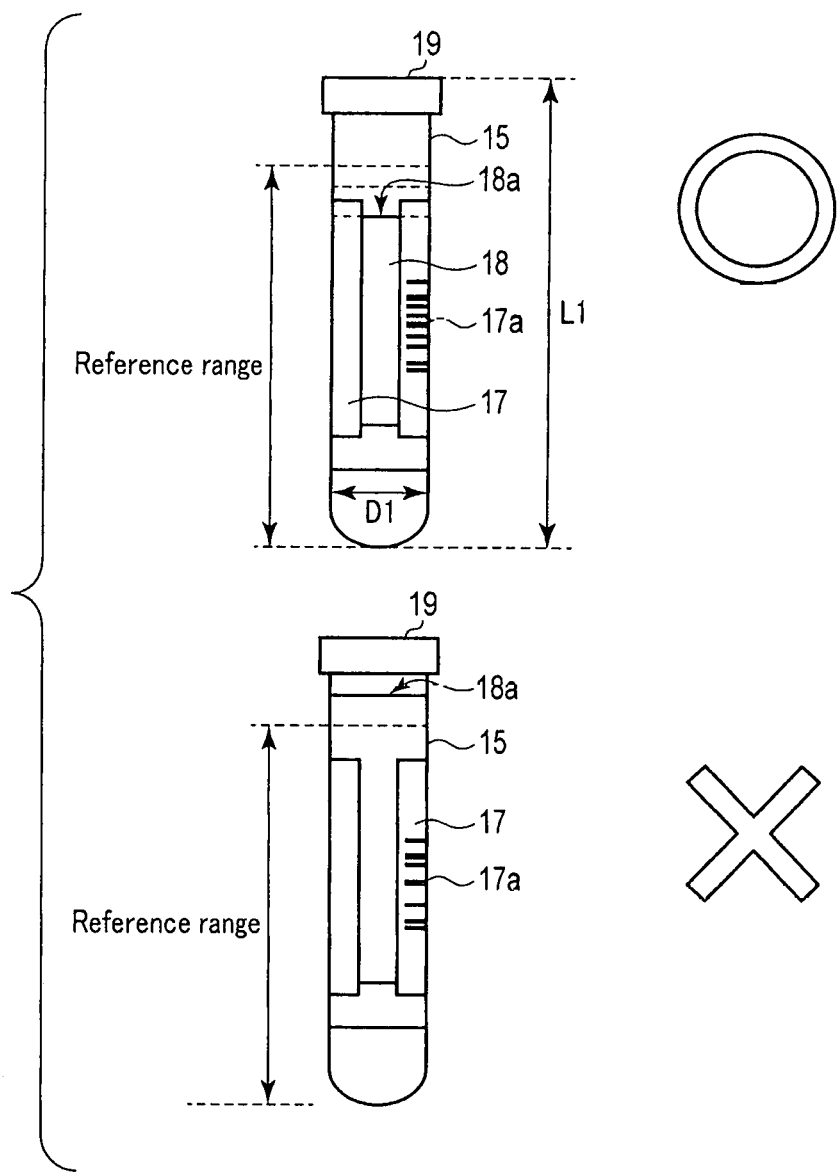
FIG. 5 is an explanatory drawing of a liquid level determination process in the sorting process.

FIG. 4 is an explanatory drawing of the matching determination for the sample containers 15, and it shows a result of detection of types and display information for a plurality of targets T1 to T6 and a determination result based on the types and display information. FIG. 5 is an explanatory drawing of the liquid level determination for the sample containers 15, and it shows the exterior of the targets T7 and T8 and a determination result based on the exterior.

As shown in FIGS. 4 and 5, the sample container 15 is, for example, a blood sample tube made of transparent glass having a tube shape, and it has a cylindrical shape having a cylindrical space inside for storing a sample 18, such as blood serum, and has a top opening. A stopper 19 is provided at the top opening. Various types can be used for the sample container 15, and a test item is set in accordance with a type of the sample container 15. As shown as an example in FIG. 4, the types of the sample containers 15 are set in correspondence to exterior characteristics of the sample containers 15, and the types are classified by, for example exterior characteristics such as shapes, dimensions, and colors, etc. of the containers. In the present embodiment, the type is distinguished by, for example, a tube diameter and a tube length of a blood test tube, and a shape and color of a stopper.

A label 17, for example, is adhesively affixed on the outer side surface of the sample container 15. On the label 17, a bar code 17a is displayed as an information display portion indicating a variety of information such as identification information, etc. of the sample. The bar code 17a includes information indicating a test item that the sample 18 in the sample container 15 is to be subjected to.

The sample 18 in the sample container 15 consists of a blood clot layer, a separator (silicon) layer, and a blood serum layer, separated and arranged from the bottom in this order. The top surface of a blood serum layer is a liquid level 18a of the sample 18.

The stopper 19 is attached to the top opening of the sample container 15. Various types are used for the stopper 19, for example, and the stopper 19 is attached in accordance with a test item.

Accordingly, in a normal sample container 15, test item information on the label 17 matches the test item information by the tube type.

The position sensor 23 detects the arrival of the sample container 15, which is sent one after another, to the imaging position P2, and sends the detected information to the CPU 52.

The rotation mechanism 24 is an apparatus for rotating the sample container 15 by rotating the holder 16, and comprises: a rotation motor which is, for example, rotatively driven by the control at the CPU 52, a rotation body 15b having an outer surface abutted to the outer surface of the sample container 15 with a high friction force, and a transmission mechanism 15c which transmits the rotation of the motor to the rotation body. The rotation mechanism 24 rotates the sample container 15 at a predetermined timing during the imaging. In other words, imaging is performed while the sample container 15 is being rotated.

The imaging section 25 has an imaging sensor, such as a CCD camera, for example, and is provided on the side of the imaging position P2. The imaging section 25 takes an image of the sample container 15 from the side of the blood test tube held in a standing state at the imaging position P2 to capture image information. The captured image data is sent to the CPU 52, and stored in the storage unit 51.

The sorting unit 30 (the sample processing apparatus) comprises a carrier mechanism 21 and a transfer apparatus 31 which removes, from the test line, an erroneous sample container 15 located at the pickup position P3 on the carrier path.

The transfer apparatus 31 comprises a transfer mechanism which grips the sample container 15 which is a target for sorting and transfers it outside of the test line. The transfer apparatus 31 is driven at a certain timing by the control by the CPU 52, for example, and it removes the error sample container 51 from the carrier path by the operation of transferring the sample container 15. Specifically, the transfer apparatus 31 grips the erroneous sample container 15 on the carrier path using the transfer mechanism, removes the erroneous sample container 15 from the test line, and, for example, transfers it to an error position P4 off of the carrier path.

Since the sorting unit 30 is controlled to not transfer non-error sample containers 15, a non-error sample container 15 is directly sent, by the carrier mechanism 21, to the continuation unit 40 which continues to the biochemical test line 14a.

The continuation unit 40 is a processing unit provided on the downstream side of the sorting unit 30, and it comprises a carrier mechanism 21 having a carrier path continuing the biochemical line 14a, for example, and carries the holder 16 holding the sample container 15 coming from the storing unit 30 to the downstream side by the operation of the carrier mechanism 21.

The storage section 51 stores various data including position information and image information of the sample container 15. For example, the stored image of the sample container 15, taken at the imaging position P2 at an initial stage after the loading, may be used at an initial state check when any problem occurs at a later process.

The CPU 52 performs data processing, such as computation and determination, including image processing, based on the various data. Specifically, by image processing on a taken image, the CPU 52 detects a type of the sample container 15 from the exterior information, such as the tube diameter and tube length of the sample container 15, and the shape and color of the stopper 19, based on information of brightness, chroma, color phase, and tone. The CPU 52 also detects information of the bar code 17a from a taken image by image processing. The bar code 17a, for example, includes identification information of the sample and information, such as target test items. The CPU 52 detects a position of the blood serum surface, that is, a liquid level of the sample 18, from the image of the sample container 15.

The CPU 52 makes a determination based on the detection information and the information of the bar code 17*a* which is display information, and a tube type. Specifically, if some information related to a type of the sample container 15 and some information of the bar code 17*a* are different from a verification example, an error determination is made. Therefore, it is determined whether or not the test items based on the bar code 17*a* and the test items based on the tube type match, and if it is determined that the test items distinguished, for example, by the tube type do not match the test items displayed on the bar code 17*a* affixed to the same sample container 15, an error determination is made.

Furthermore, the CPU 52 performs a liquid level determination process to determine whether or not the top edge position of the surface of the blood serum, which is the sample 18, in other words, the liquid level of the sample 18, falls under a predetermined reference range. If the detected liquid level does not fall under the reference range, the CPU 52 makes an error determination; if the detected liquid level falls under the reference range, the CPU 52 determines no error. For example, the reference range is set with reference to a liquid level where the possibility of contamination is low. In other words, the sample container 15 with a high liquid level beyond the reference range and a high contamination possibility is removed from the test line 14 by the CPU 52 at an initial stage so that a spray can be avoided.

The CPU 52 controls the operation of each of the structural elements based on the various data and the calculation and determination results. Specifically, the carrier mechanism 21 is operated at a predetermined timing to perform carrying. The CPU 52 controls the operation of the imaging section 25 to have the imaging section 25 perform an imaging process at a predetermined timing. The CPU 52 controls the operation of the transfer apparatus 31 in accordance with each determination result. For example, in the present embodiment, the CPU 52 drives the transfer mechanism of the move apparatus 31 so that a sample container 15 determined to be erroneous, that is, a sample container 15 in which the tube type and the test item of the bar code 17*a* do not match, or a sample container 15 in which the liquid level is beyond the reference range, is classified into an error line and is removed from the test target.

In the following, the flow of the CPU 52 in the test preprocessing method according to the present embodiment is explained with respect to FIG. 3.

When it is detected that the sample container 15 arrives at a predetermined imaging position P2 (ST1), the CPU 52 controls the image capture unit 20 to perform an imaging process. Specifically, the CPU 52 drives the rotation mechanism 24 (ST2) to rotate the sample container 15, and controls the imaging unit 25 to perform an imaging process (ST3). The imaging unit 25 takes an image of the sample container 15 in a standing state from a plurality of angles from the side to capture an image. At this time, an image of the entire periphery of the sample container 15 can be acquired because the sample container is rotated. The CPU 52 is then stores data of the acquired image in the storage section 51 (ST4).

Next, the CPU 52 performs the calculation and determination processes. Specifically, an image processing, in other words image analysis, is performed based on the image data of the sample container 15 to detect identification information displayed on the bar code 17*a* as display information (ST5).

The CPU 52 determines a tube type based on the image processing, that is, image analysis of the same image. Herein, the tube type is detected using a tube length L1 and the tube diameter D1 of the sample container 15, and a stopper type based on the shape and color of the stopper 19 as information used to determine the tube type (ST6).

Then, it is determined whether or not the test items indicated by the bar code 17*a*, for example, and the test items indicated by the tube type match (ST7). For example, if the test items indicated by the bar code 17*a* and the test items indicated by the tube type do not match, an error is determined and the process proceeds to ST10. In the present embodiment, if any of the exterior characteristics related to a tube type, in other words, tube length, tube diameter, and stopper type, etc. do not match with a verification example, an error is determined.

In the present embodiment, as shown in FIG. 4, an example will be described where it is determined whether or not information of the bar code 17*a* and various information related to a tube type matches with a preset verification example for one of the plurality of test lines 14*a* to 14*c*, for example the biochemical test line 14*a*; and if the information does not match, an error is determined. Specifically, as shown in FIG. 4 for example, in the verification example of the biochemical test, the height (the tube length) is 100 mm, the diameter is 16 mm, and the stopper type is a green rubber stopper, and when the bar code data indicates 0001, if any items in the detection information do not match with any items in the verification example, an error is determined.

The CPU 52 detects, from the same image by an image processing, i. e. an image analysis (ST8), a position of the liquid level 18*a* of the sample 18, in other words, the top edge position information of the sample 18. If the liquid level 18*a* is determined to be higher than a reference range based on the top edge position information, an error is determined, and the process proceeds to ST10.

At ST10, as an error processing, the sample container 15 determined to be erroneous is sorted to be removed from the test line 14. Specifically, in the sorting unit 30, the control of the CPU 52 drives the transfer apparatus 31 and transfers the erroneous sample container 15 to the error position P4 outside of the test line 14. In other words, the determined sample container 15 is transferred to a rack located at the error position P4, for example, by the transfer mechanism of the transfer apparatus 31.

On the other hand, a sample container 15 that is determined to not be erroneous, in other words, a normal sample container 15, is sent to the continuation unit 40, for example, as a normal processing (ST11). A variety of processes, such as opening and dispensing, are performed on the normal sample container 15 through various processing apparatus provided in the downstream, and the sample container 15 is guided to an analyzer corresponding to the test item. Then, the CPU 52 repeats the process from ST1 to ST12 for a plurality of the sample containers 15, which are subsequently sent, until an end instruction is made (ST12).

According to the sample processing apparatus and the sample processing method according to the present embodiment, it is possible to improve the accuracy of sorting by verifying, as preprocessing prior to the test, the test items included in the display information of the bar code 17*a* with the features of the sample container 15 corresponding to the test items, and removing a mismatching sample container 15 from the targets for testing.

It is possible to prevent splashes by distinguishing a sample container 15 having a high possibility of contamination due to the position of the liquid level 18*a*.

According to the present embodiment, it becomes possible to use image data acquired and stored at an initial stage prior to the test processing, in order to check the initial status when any problems occur at a later stage of the processing.

It is possible to perform detection quickly and accurately in a plurality of determinations, such as matching a determination on test items and a liquid level determination by using a common image to perform an image analysis.

In the above-described embodiment, it is possible to increase and decrease the number of units by arranging the connection of a plurality of units; thus, the present embodiment is versatile and applicable to any conventional apparatus.

The present invention is not simply limited to each of the above-described embodiments; the present invention can be realized by transforming the constituent elements within the range without deviating from the main concept of the present invention. For example, in the above-described embodiment, a sample processing is performed for each of the sample containers; however, the process can be performed concurrently on a plurality of the sample containers 15.

In the present embodiment, as a tube type, a tube diameter, a tube length, and a stopper type are detected as a reference for determination; however, any of the items can be omitted, and any other items can be added. For example, a stopper type can be omitted.

A bar code type is not limited, and various types of bar codes are applicable. Furthermore, in the above-described embodiment, the display information is detected from a bar code affixed to a sample container 15, but is not limited thereto; other types of display information may be used.

In the above-described embodiment, an error is determined when any of display information and a types does not match with a verification example, an error is determined but not limited thereto, and sorting may be carried out based on type only; for example, when a cap is blue, a container is determined as normal, and when a cap is read, a container is determined as erroneous, and so on.

The sorting process may be performed based on a correspondence between display information and a type. For example, if a classification indicated by display information does not match with a classification by a type, a sample container is determined to be normal, and if does not match, a sample container is determined to be erroneous.

The mechanism of the transfer apparatus in the sorting unit is not limited to the above-described transfer mechanism. For example, a mechanism provided with a rotatable guide blade in a carrier line which restricts a carrier direction by adjusting the angle of the guide blade by the control at the CPU 52 to sort the sample containers into different lanes.

For the sake of explanation, an example of performing a matching determination for the biochemical test line 14a which is one test item of a plurality of test lines is explained in the above embodiment but is not limited thereto; a matching determination can be made concurrently for a plurality of test lines. For example, if there are a plurality of test items, a tube type and display information corresponding to each test item is stored or set as a verification example, and if both of the type and the display information detected from an image of a sample container match with a verification example of any of the test lines, the sample container is sorted into and carried to the test line. On the other hand, if any of the tube types and the display information detected from an image of a sample container does not match with a verification example, a sorting unit is controlled to remove the sample container from the carrier line.

Each unit is interchangeable as needed. The sorting apparatus 10A shown in FIG. 6A as another embodiment, for example, is connected to a unit 60 comprising a carrier mechanism 21, a transfer apparatus 31, and an error rack 32 on the downstream of the image capture unit 20, and may be configured to move a sample container 15 as an error to the error rack 32 which is arranged at a position off of a carrier path that is followed by the test line.

Furthermore, in the above-described embodiment, an example where a plurality of units are connected and arranged is explained, but the embodiment is not limited thereto; the embodiment may be configured as a single apparatus.

Furthermore, a type and a state of the sample is not limited to the above embodiment; it may be a gel, for example.

Any constituent element illustrated in the above-described embodiment may be omitted, and the shape, structure, material, etc. of each constituent element may be changed. A combination of a plurality of constituent elements disclosed in the above-described embodiment can constitute various inventions.

The invention claimed is:

1. A sample processing apparatus, comprising:
an image capture unit which has a first conveyor-type carrier mechanism for carrying a holder that is provided along a predetermined carrier path and holds a sample container storing a sample inside thereof in a standing state, the first conveyor-type carrier mechanism being provided on a top of the sample processing apparatus, the image capture unit comprising
an imaging unit comprising an image sensor that obtains an image of the sample container on the carrier mechanism from one side of an imaging position on the carrier path; and
a rotation mechanism comprising a rotation body that rotates the sample container by being rotated, the rotation mechanism being provided on an other side of the imaging position on the carrier path;
a sorting unit comprising a second conveyor-type carrier mechanism for carrying the sample container held in the holder in a standing state, the second conveyor-type mechanism being arranged on the top of the sample processing apparatus and successively provided downstream of the carrier path of the image capture unit, and a moving device that moves the sample container on the carrier mechanism; and
a control unit configured to
obtain an image of the sample container at the imaging position by causing the imaging unit to take an image of the sample container from a plurality of angles from the side by the imaging unit while the sample container being held in a standing state in the carrier path and being rotated by rotation of the rotation body,
detect, based on exterior information of the sample container detected by an image processing from an image of the sample container obtained by the imaging unit, a type of the sample container corresponding to the exterior information, a top edge position information of a sample in the sample container, and display information displayed on the sample container, and control an operation of the moving device based on the type, the top edge position information, and the display information, wherein
each of the conveyor-type carrier mechanisms comprises a pair of guide rails provided along the carrier path, and a carrier belt arranged along the carrier path,
the holder engages the pair of guide rails and is supported in a standing state by the engagement, and the image capture unit and the sorting unit are configured as separate apparatuses, and the carrier paths thereof are arranged so as to be continuous.

2. The sample processing apparatus according to claim 1, wherein
the apparatus comprises a plurality of lines,
the type is set in correspondence to the exterior information, and
the control unit is configured to control the sorting unit to sort the sample container to a line determined based on the type, the display information, and the top edge position information.

3. The sample processing apparatus according to claim 2, wherein the control unit is configured to detect the display information from a bar code affixed to the sample container, and when a test item corresponding to the display information and a test item corresponding to the type do not match, the control unit is configured to control the sorting unit to determine the sample container to be erroneous and to remove the erroneous sample container from a test line corresponding to the test item.

4. The sample processing apparatus to claim 3, wherein the control unit is configured to make an error determination when the detected exterior information of the sample container is different from a verification example, or when the detected top edge position does not fall under a predetermined reference range.

5. The sample processing apparatus according to claim 1, wherein
the sample container is a blood test tube configured in a cylindrical shape and has an opening to which a stopper is attached, and
the exterior information includes, at least one of a length, a width, a diameter of the blood test tube, a shape of the stopper, or a color of the stopper which are detected by an image processing on the image.

6. The sample processing method according to claim 1, wherein the control unit acquires an image of an entire periphery of the sample container.

7. The sample processing apparatus to claim 1 further comprising
a transfer apparatus comprising a transfer mechanism which grips and transfers the sample container.

8. The sample processing apparatus according to claim 1, wherein the control unit comprises a CPU.

9. The sample processing apparatus according to claim 8, wherein the control unit is configured to detect the type, the top edge position, and display information displayed on the sample container based on the image of the sample container, and is configured to perform a sorting process based on the type, the top edge position information, and the display information.

10. The sample processing apparatus according to claim 9, wherein the control unit is configured to make an error determination, if one of the exterior information and the display information is different from a verification example, or the detected liquid level does not fall under a predetermined reference range.

11. The sample processing apparatus according to claim 8, wherein the control unit is configured to make an error determination, if the exterior information of the sample container is different from a verification example, or the detected top position does not fall under a predetermined reference range.

12. The sample processing apparatus according to claim 8, wherein
the image of the sample container is captured before a test, and
a stopper is attached to the sample container.

* * * * *